United States Patent [19]

York

[11] Patent Number: 5,061,696
[45] Date of Patent: Oct. 29, 1991

[54] HYPOTONIC COMPOSITIONS FOR SELECTIVELY KILLING UNDESIRABLE LENS CELLS IN THE HUMAN EYE AND METHODS FOR USING SUCH COMPOSITIONS

[76] Inventor: Kenneth K. York, 2300 N. Edgemont, Los Angeles, Calif. 90027

[21] Appl. No.: 353,828

[22] Filed: May 18, 1989

[51] Int. Cl.$^5$ ............................................. A61K 31/715
[52] U.S. Cl. ........................................ 514/54; 514/912
[58] Field of Search ...................... 514/54, 912; 424/78

[56] References Cited

U.S. PATENT DOCUMENTS 4,486,416 12/1984 Stoll et al. ............................ 514/912

Primary Examiner—Frederick E. Waddell
Assistant Examiner—Zohreh A. Fay

[57] ABSTRACT

A hypotonic composition for selectively destroying lens cells in humans and other mammals such as lens epithelial cells that would otherwise cause clouding of the lens capsule after removal of the lens from the capsule includes one or more ocularly biocompatible viscoelastic substances that have the capacity for destroying such cells osmotically in small concentrations in hypotonic aqueous solutions, yet are sufficiently viscoelastic to attack only tissues to which they are applied without leaking or otherwise flowing onto the damaging adjacent and neighboring tissue. Such compositions are placed intraocularly in the lens capsule by applying a sufficient quantity of the composition to the epithelial cells to be destroyed to destroy them without damaging or otherwise destroying neighboring eye tissue.

6 Claims, No Drawings

HYPOTONIC COMPOSITIONS FOR SELECTIVELY KILLING UNDESIRABLE LENS CELLS IN THE HUMAN EYE AND METHODS FOR USING SUCH COMPOSITIONS

This invention relates to hypotonic compositions for selectively destroying lens tissue in the human eye that causes clouding of the lens capsule after removal of the lens nucleus and cortex from the capsule, and to methods for utilizing such compositions for this purpose. These compositions comprise, in preferred embodiments, a hypotonic, viscoelastic, ocularly biocompatible substance such as sodium hyaluronate, chondroitin sulfate, hydroxypropylmethylcellulose, collagen, polyacrylamide and mixtures of these and/or other ocularly biocompatible viscoelastic compounds. Most preferably, these compositions include very high molecular weight, cross-linked hyaluronic acid, preferably with concentrations of 0.3% or less of this substance in distilled water or a hypotonic aqueous solution. In preferred embodiments, the molecular weight of these high molecular weight substances is greater than about two million.

These compositions are formed by mixing one or more of the ocularly biocompatible viscoelastic substances with distilled water in amounts sufficient to create a hypotonic viscoelastic solution that kills lens epithelial cells that cause clouding of the lens capsule after removal of the lens from the capsule. These compositions preferably contain small enough concentrations of these ocularly biocompatible viscoelastic substances to osmotically swell and rupture such epithelial lens cells, yet enough viscoelasticity such that the solution behaves as a gel, can be easily applied into the lens capsule in the eye with a cannula and will remain there for at least a few minutes without contacting other tissues. These compositions must be sufficiently viscous that they ca be placed directly on epithelial lens cells to be killed without leaking or otherwise flowing onto healthy cells that are not to be destroyed. Such compositions permit accurate, safe and prolonged placement of the hypotonic composition on epithelial lens cells in humans and other mammals to be killed without endangering adjacent healthy tissues.

The hypotonic compositions of this invention are preferably used by applying the compositions, intraocularly, directly to lens epithelial cells in humans or other mammals, using a cannula and syringe or other focal delivery system. These compositions are applied to the lens tissue to be killed in amounts sufficient to destroy epithelial lens cells that would otherwise cause clouding of the lens capsule after removal of the lens from the capsule. In most instances, the lens capsule would be largely filled.

This technique is preferably done in combination with anterior capsulotomy techniques that create a small opening in the anterior capsule such as capsulorhexis. In a preferred technique for application, air or another gas would be inserted into the lens capsule while the aqueous fluid was displaced or aspirated simultaneously.

This technique can include the steps of: aspirating all of the aqueous and/or irrigating solution from the anterior chamber, posterior chamber and lens capsule after cataract extraction; replacing these solutions with an ocularly biocompatible gas such as sterile air; and then applying one of the compositions of this invention to the epithelial cells to be destroyed. Alternatively, this technique can include the steps of: using a double cannula for simultaneously aspirating all of the aqueous and/or irrigating solution from the lens capsule, posterior chamber and anterior chamber; while injecting an ocularly biocompatible gas into the lens capsule posterior chamber and anterior chamber, filling them with the gas; and then applying one of the compositions of this invention to the cells to be destroyed using a separate cannula.

Once the eye has been filled with a gas, preferably an ocularly biocompatible gas such as air, the hyoptonic viscoelastic composition can easily be injected via a cannula to fill the lens capsule. By filling the lens capsule with gas first, the hypotonic viscoelastic does not become diluted with aqueous and/or irrigating solution, and lose its hypotonicity. After placement of these compositions on the cells to be destroyed, the composition can be removed, for example, by aspiration through a syringe, and the remaining composition can be diluted with an isotonic solution. In these methods, the compositions are applied to the lens epithelial cells to be destroyed in amounts sufficient to destroy them in a relatively short period of time. In a preferred embodiment, a hypotonic viscoelastic solution would be combined with an ocularly biocompatible dye or chromophore, preferably of large molecular weight, and/or chemically bound, to minimize diffusion so that the viscoelastic can be easily identified, and readily and adequately removed.

What is claimed is:

1. A method for destroying lens epithelial cells comprising applying directly to said cells, in an amount sufficient to destroy said cells, a composition including at least one ocularly biocompatible viscoelastic substance that has the capacity to osmotically swell and rupture said cells without damaging or destroying tissues adjacent to said cells.

2. A method for destroying lens epithelial cells comprising aspirating all of the aqueous and/or irrigating solution from the anterior chamber, posterior chamber and lens capsule after cataract extraction, and replacing said solutions with an ocularly biocompatible gas, and then applying, directly to said cells, in an amount sufficient to destroy said cells in the lens capsule, a composition including at least one ocularly biocompatible hypotonic viscoelastic substance that has the capacity to osmotically swell and rupture said cells without damaging or destroying adjacent tissues.

3. A method for destroying lens epithelial cells comprising using a double cannula for simultaneously aspirating aqueous and/or irrigating solution from the lens capsule, posterior chamber and anterior chamber, injecting an ocularly biocompatible gas to fill the anterior chamber, posterior chamber and lens capsule with said gas, and then injecting via a separate cannula, a hypotonic viscoelastic substance to fill the lens capsule and osmotically destroy the lens epithelial cells without diluting the hypotonic viscoelastic with isotonic solutions in the eye.

4. The method of claim 1 further comprising selecting, as the ocularly biocampatible viscoelectric substance, a substance selected from the group consisting of high molecular weight cross-linked hyaluronic acid with a molecular weight in excess of 2 million having a concentration of water of about 0.3% by weight of less, sodium hyaluronate, chondroitin sulfate, hydroxypropylmethicellulose, collagen, polyacrylamide and mixtures of two or more members of this group.

5. The method of claim 2 further comprising selecting, as the ocularly biocampatible viscoelastic substance, a substance selected from the group consisting of high molecular weight cross-linked hyaluronic acid with a molecular weight in excess of two million having a concentration of water of about 0.3% by weight or less, sodium hyaluronate, chondroitin sulfate, hydroxypyropylethicellolose, collagen, polyacrylamide and mixtures of two or more members of this group.

6. The method of claim 3 further comprising selecting, as the ocularly biocompatible viscoelastic substance, a substance selected from the group consisting of high molecular weight cross-linked hyaluronic acid with a molecular weight in excess of 2 million having a concentration of water of about 0.3% by weight or less, sodium hyaluronate, chondroitin sulfate, hydroxypropylmethlcellulose, collagen, polyacrylamide and mixtures of two or more members of this group.

* * * * *